(12) United States Patent
Ellwein et al.

(10) Patent No.: US 10,151,617 B2
(45) Date of Patent: Dec. 11, 2018

(54) METHOD AND DEVICE FOR MONITORING AN OIL LEVEL IN A MACHINE

(71) Applicant: Kriwan Industrie-Elektronik GmbH, Forchtenberg (DE)

(72) Inventors: Christian Ellwein, Schwäbisch Hall (DE); Christoph Leja, Künzelsau (DE); Franz Stoll, Pfedelbach (DE)

(73) Assignee: KRIWAN INDUSTRIE-ELEKTRONIK GMBH, Forchtenberg (DE)

( * ) Notice: Subject to any disclaimer, the term of this patent is extended or adjusted under 35 U.S.C. 154(b) by 0 days.

(21) Appl. No.: 15/672,372

(22) Filed: Aug. 9, 2017

(65) Prior Publication Data

US 2018/0052034 A1    Feb. 22, 2018

(30) Foreign Application Priority Data

Aug. 17, 2016  (DE) .................... 10 2016 115 228

(51) Int. Cl.
*G01N 33/28*  (2006.01)
*G01F 23/292*  (2006.01)
(Continued)

(52) U.S. Cl.
CPC ......... *G01F 23/2925* (2013.01); *F01M 11/06* (2013.01); *F01M 11/061* (2013.01); *G01F 23/2922* (2013.01); *G01N 21/15* (2013.01); *G01N 21/431* (2013.01); *G01N 21/552* (2013.01); *F01M 2011/0433* (2013.01); *G01N 21/4133* (2013.01); *G01N 2021/157* (2013.01); *G01N 2021/434* (2013.01)

(58) Field of Classification Search
CPC ............ G01F 23/2925; G01F 23/2922; G01N 21/4133; F01M 11/06
USPC .......................................................... 356/70
See application file for complete search history.

(56) References Cited

U.S. PATENT DOCUMENTS

| | | | | |
|---|---|---|---|---|
| 4,898,462 A | * | 2/1990 | Numata | G01N 21/27 250/573 |
| 5,005,005 A | * | 4/1991 | Brossia | B64D 15/20 250/573 |

(Continued)

FOREIGN PATENT DOCUMENTS

GB          20366326 A      6/1980

*Primary Examiner* — Sunghee Y Gray
(74) *Attorney, Agent, or Firm* — Renner Kenner Greive Bobak Taylor & Weber

(57) ABSTRACT

A method for monitoring an oil level in a machine includes transmitting a light beam into an optical system to be reflected or refracted to a receiver to generate a reception signal. The light beam is emitted at a set transmission power, and an oil deficiency is recognized when the reception signal exceeds a predefined level value. The transmission power of the light beam is settable between a minimum and a maximum transmission power, and contamination of the optical system is analyzed by: (a) the transmitter transmits a first light beam at the maximum transmission power to generate a first reception signal, and (b) analyzing the difference between the first reception signal and a second reception signal generated by a light beam at less than the maximum transmission power, the magnitude of the difference representing a measure of the degree of contamination of the optical system.

9 Claims, 5 Drawing Sheets

(51) Int. Cl.
*F01M 11/06* (2006.01)
*G01N 21/15* (2006.01)
*G01N 21/43* (2006.01)
*G01N 21/552* (2014.01)
G01N 21/41 (2006.01)
F01M 11/04 (2006.01)

(56) References Cited

U.S. PATENT DOCUMENTS 5,452,076 A 9/1995 Schopper
6,151,108 A * 11/2000 Kwon .................... G01N 15/06
356/338

* cited by examiner

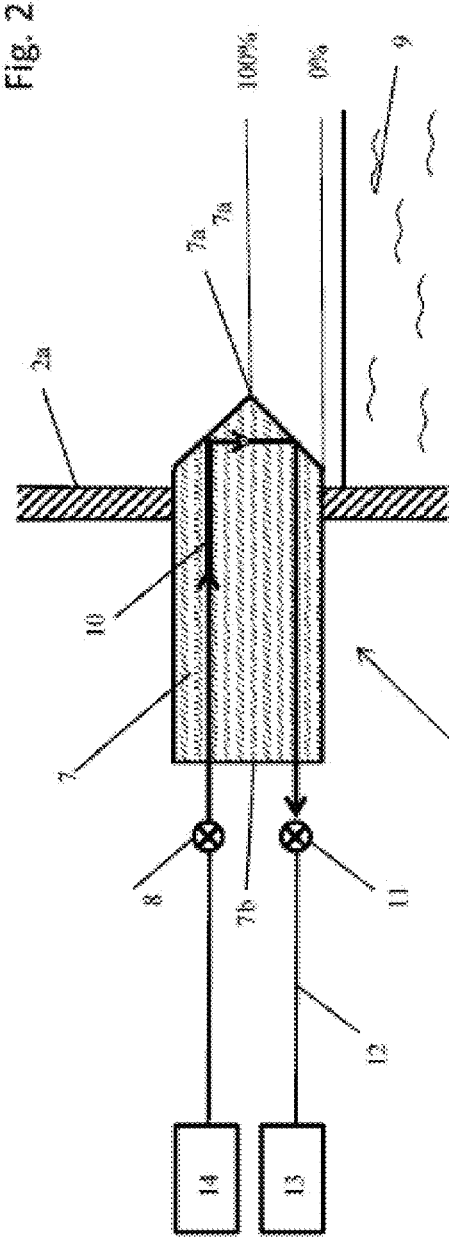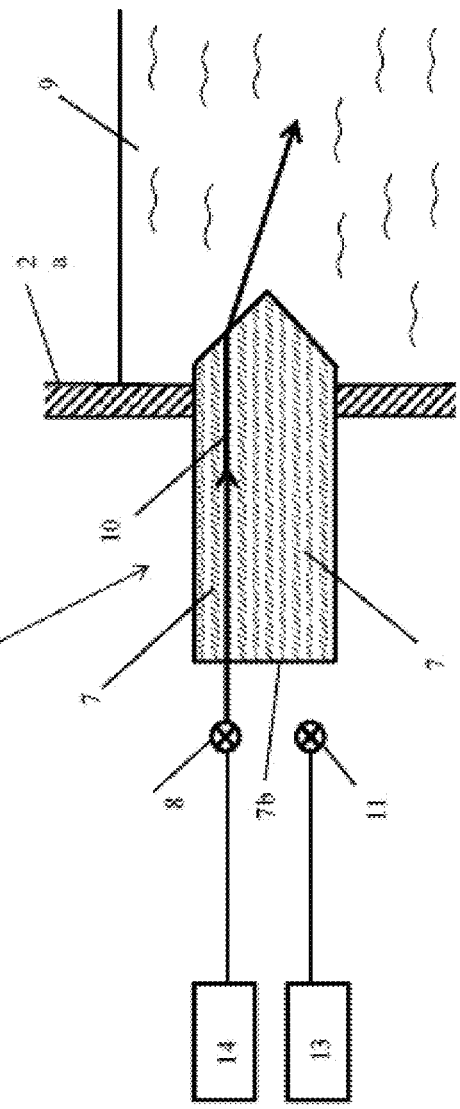

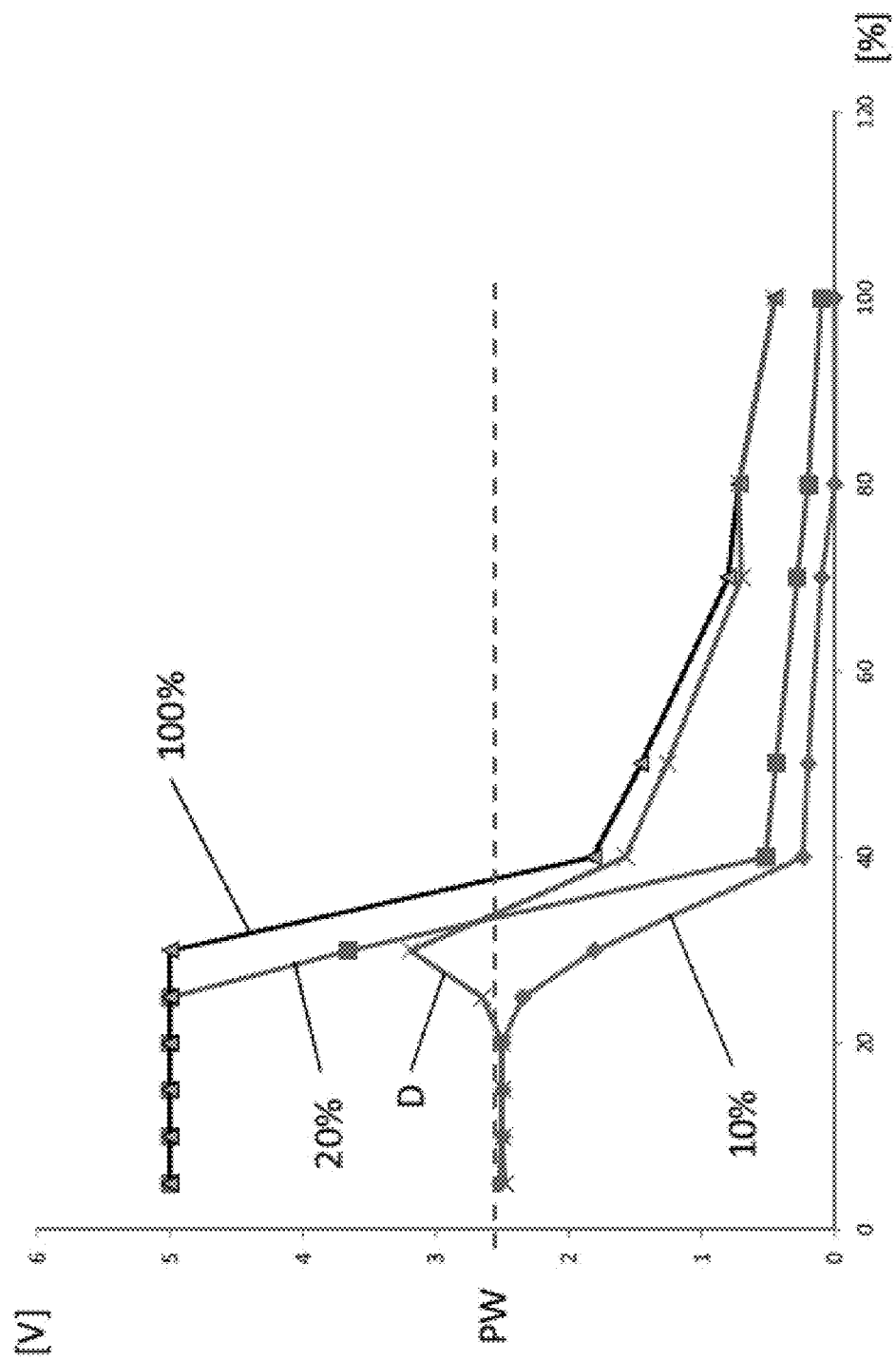

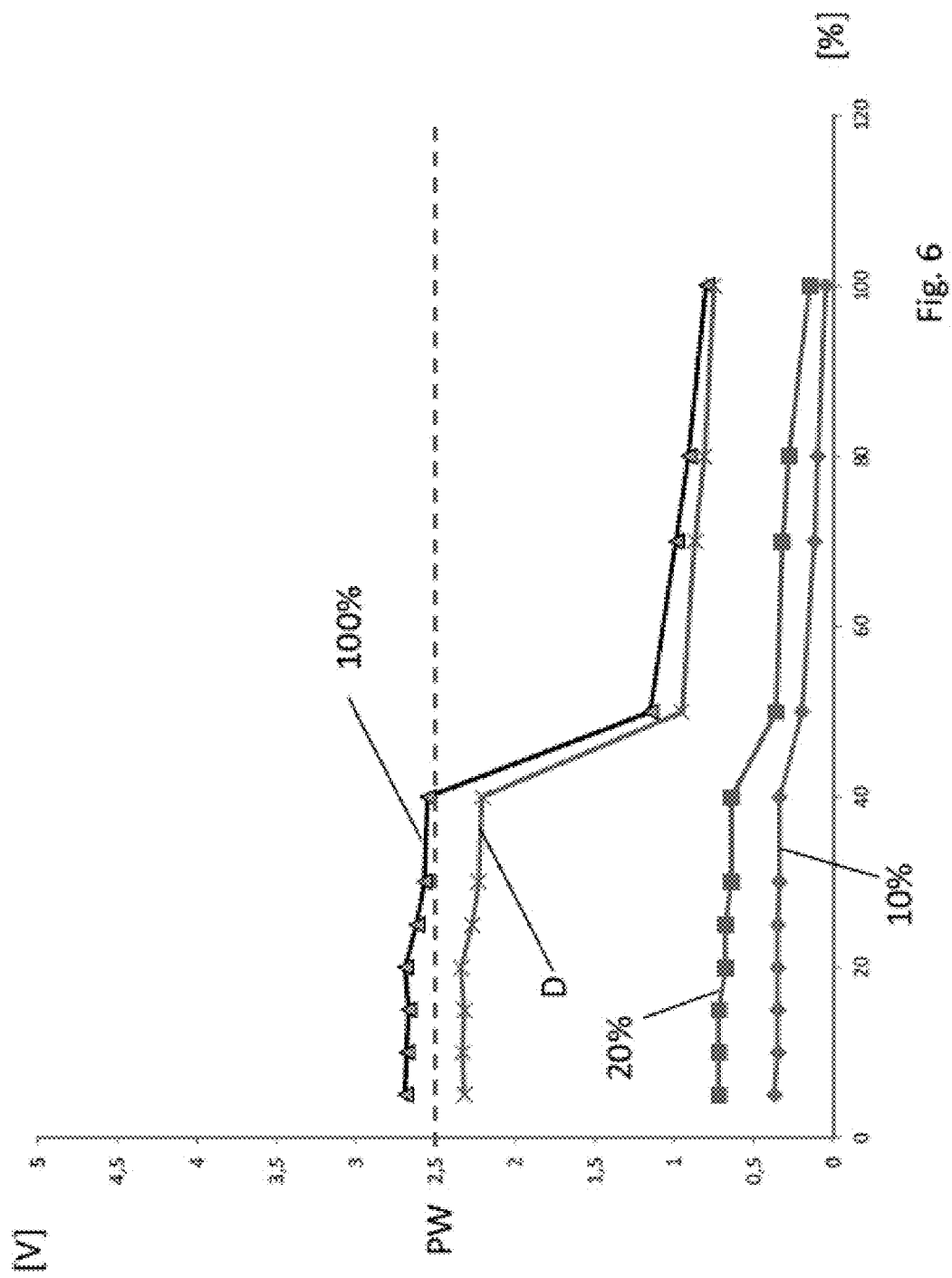

METHOD AND DEVICE FOR MONITORING AN OIL LEVEL IN A MACHINE

TECHNICAL FIELD

The invention relates to the monitoring of an oil level in a machine by means of an optical sensor, wherein a transmitter transmits a light beam into an optical system, and the light beam is reflected or refracted by the optical system, as a function of the oil level to be monitored, to a receiver, where a reception signal is generated, the light beam being emitted at a set transmission power during the monitoring operation, and an oil deficiency being recognized when the reception signal exceeds a predefined level value.

BACKGROUND

For this method, a so-called oil level regulator is used which monitors the oil level in a machine, for example a compressor, and refills oil from a reservoir as soon as an oil deficiency is determined. However, the optical system used for the monitoring may become soiled over time due to a contaminant layer depositing on the optical system, and the reflection/refraction of the light beam is distorted. This is problematic in particular when the reception signal becomes so weak that it no longer reaches the predefined level value, and always reports a sufficient oil level even though in reality an oil deficiency is already present.

SUMMARY

The object of the invention, therefore, is to provide a method and a device for monitoring the oil level in a machine, thereby ensuring a more reliable monitoring operation.

This object is achieved according to the invention by claims 1 and 9.

The method according to the invention for monitoring an oil level in a machine uses an optical sensor, wherein a transmitter transmits a light beam into an optical system, and the light beam is reflected or refracted by the optical system, as a function of the oil level to be monitored, to a receiver, where a reception signal is generated, the light beam being emitted at a set transmission power during the monitoring operation, and an oil deficiency being recognized when the reception signal exceeds a predefined level value. The transmission power of the light beam is settable between a minimum and a maximum transmission power, and a check of a degree of contamination of the optical system is carried out according to the following test operation as soon as an oil deficiency is recognized:

a. the transmitter transmits a first light beam at the maximum transmission power, as the result of which a first reception signal is generated at the receiver, b. a difference between the first reception signal and a second reception signal is then formed, the second reception signal having been generated by a light beam at less than the maximum transmission power, and the magnitude of the difference representing a measure of the degree of contamination of the optical system.

The device according to the invention for monitoring an oil level in a machine has an optical sensor which includes a transmitter for transmitting a light beam into an optical system, and a receiver for receiving a reflected or refracted light beam from the optical system as a function of the oil level to be monitored, and for generating a reception signal. In addition, an evaluation device for comparing the reception signal to a predefined level value is provided, an oil deficiency being recognized when the reception signal exceeds the predefined level value. Furthermore, a power control device is provided with the transmitter for setting the transmission power of the light beam between a minimum and a maximum transmission power, and the evaluation device is provided for checking a degree of contamination of the optical system according to method steps a) and b) described above.

Due to the transmission power of the light beam being settable between a minimum and a maximum transmission power, during the test operation there is an option for checking the degree of contamination of the optical system, and thus receiving early warning of a faulty monitoring operation.

There is also the option for maintaining the monitoring operation in an even more reliable manner when a slight degree of contamination of the optical system has already begun. This is achieved by increasing the transmission power of the light beam during the monitoring operation as a function of the magnitude of the difference between the first reception signal and the second reception signal. In this way, with a clean optical system, operations may be carried out at a comparatively low transmission power, for example 10% transmission power, thus saving on operating costs. Only when a certain degree of contamination is recognized during the test operation is it possible to continue to maintain a reliable monitoring operation by increasing the transmission power during the monitoring operation. Cleaning of the optical system is advantageously not carried out until the difference between the first reception signal and the second reception signal is less than a predefined value.

According to one preferred embodiment of the invention, the reception signal with which an oil deficiency has been recognized during the monitoring operation is used as the second reception signal during the test operation. In addition, it is provided that in the event of a determined oil deficiency, the oil level in the machine is increased by refilling with oil after carrying out the test operation.

It may optionally also be provided that the test operation is carried out even when no oil deficiency is measured during the monitoring operation, but a set time period has elapsed since the last determined oil deficiency. The test operation may thus be carried out routinely, for example after one hour. In particular a high level of contamination of the optical system that is already present while the machine is running may thus be recognized.

Another option is to carry out the test operation even when no oil deficiency is measured during the monitoring operation, but a time interval since the last oil refill, in comparison to the time intervals between two oil refills that have occurred in the past, exceeds a set limit value. This also serves as a safety measure via which a high level of contamination of the optical system that occurs suddenly between two test operation phases may be recognized. It may also be provided to use an average value of a predefined number of time intervals that have most recently occurred in the past for the comparison to the time intervals that have occurred in the past.

BRIEF DESCRIPTION OF THE DRAWINGS

Further embodiments of the invention are explained in greater detail below with reference to the following description and the drawings, which show the following:

FIG. 2 shows a schematic detailed view of the optical sensor in the event of an oil deficiency, FIG. 3 shows a schematic detailed view of the optical sensor when the oil level is sufficient, FIG. 5 shows a diagram with characteristic curves of reception signals based on different transmission powers, for a slightly contaminated optical system, and FIG. 6 shows a diagram with characteristic curves of reception signals based on different transmission powers, for a highly contaminated optical system.

DETAILED DESCRIPTION

Figure 1:
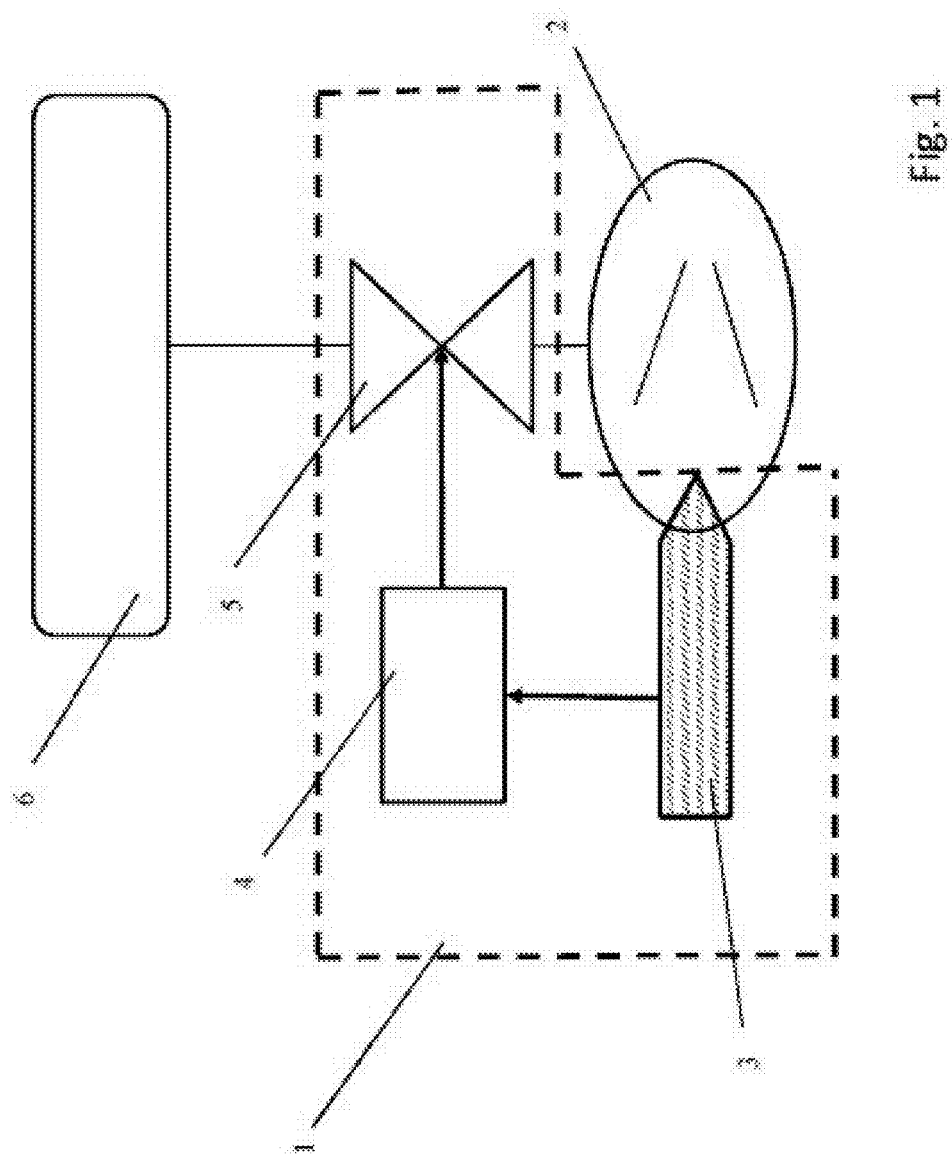
FIG. 1 shows a schematic illustration of a device according to the invention for monitoring an oil level.

The device illustrated in FIG. 1 for monitoring an oil level in a machine 2 is formed by an oil level regulator 1. The machine 2 is a compressor, for example. The task of the oil level regulator 1 is to refill the machine 2 with oil from an oil reservoir 6 in the event of an oil deficiency. For this purpose, the oil level regulator 1 has an optical sensor 3 that measures the oil level in the machine 2. If an oil deficiency is determined, a controller 4 opens a solenoid valve 5 in order to fill the machine 2 with oil from the reservoir 6.

The measuring principle of the optical sensor 3 is explained in greater detail below with reference to FIGS. 2 and 3. The optical sensor 3 has an optical reflective body 7 which is designed as a glass cone, for example, and which with a conical tip 7a protrudes into a container 2a of the machine 2. The oil 9 to be monitored is present in the container 2a. At an end 7b opposite from the conical tip 7a of the optical reflective body 7, a light beam 10 is irradiated via an optical transmitter 8 into the optical reflective body 7. After the level of the oil 9 to be monitored is below the optical reflective body 7 in FIG. 2, total reflection of the irradiated light beam 10 takes place at the conical tip 7a of the optical reflective body 7, so that the reflected light beam exits the optical reflective body at the opposite end 7b and strikes an optical receiver 11, and that location is detected as a reception signal 12.

The reception signal 12 is compared to a predefined level value in an evaluation device 13. If the oil level is too low, as shown in FIG. 2, a sufficiently large reception signal 12 reaches the receiver 11, so that the predefined level value is exceeded and the oil deficiency is thus recognized. In the situation illustrated in FIG. 3, the conical tip 7a of the optical reflective body 7 protruding into the container 2a is situated within the oil 9 to be monitored. As a result, the light beam 10 emitted from the transmitter 8 is not reflected on the conical tip 7a, but, rather, is refracted. Thus, little or no light reaches the optical receiver 11. A reception signal at the receiver 11 which is faulty or too small is interpreted by the evaluation device 13 to mean that the oil 9 in the container 2a to be monitored has a sufficient level (a sufficient oil level).

If contamination occurs at the conical tip 7a of the optical reflective body 7, only a portion of the irradiated light beam 10 is reflected in the event of an oil deficiency. This means that the reception signal 12 becomes increasingly weaker with increasing contamination. In the extreme case, the contamination may be so great that the reception signal 12 generated at the receiver 11 in the event of an oil deficiency is below the predefined level value, and the oil deficiency can thus no longer be recognized by the evaluation unit.

By use of the method described below, it may be recognized whether the optical system, i.e., the conical tip 7a of the optical reflective body 7, is contaminated. For this purpose, the transmitter 8 is connected to a power control device 14, so that the transmission power of the irradiated light beam 10 may be set between a minimum (10%, for example) and a maximum (100%, for example) transmission power.

Figure 4:
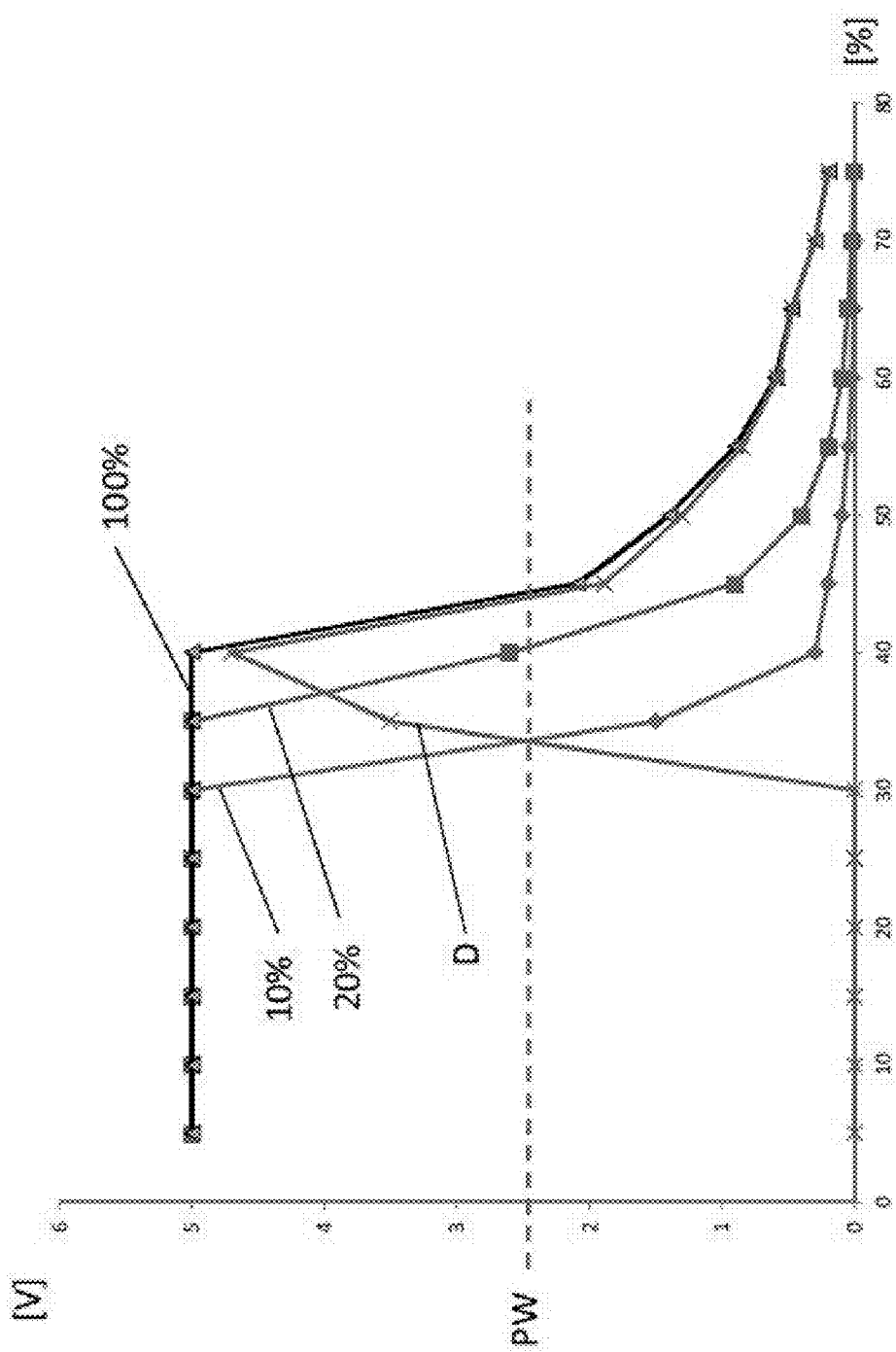
FIG. 4 shows a diagram with characteristic curves of reception signals based on different transmission powers, for a clean optical system.

FIG. 4 concerns the case of a clean optical system, and shows characteristic curves of reception signals 12 that are based on different transmission powers (10%, 20%, and 100%) of the irradiated light beam 10. The monitoring range of the oil level is plotted in percent on the abscissa. The voltage of the reception signal 12 generated at the receiver 11 is indicated on the ordinate. In the illustrated exemplary embodiment, the monitoring range of the oil level is formed by one-half the diameter of the optical reflective body 7, the conical tip indicating the oil level at a level of 100%. The lower end of the optical reflective body 7 corresponds to 0% (see FIG. 2). The monitoring range is thus situated between the tip 7a and the lower end of the optical reflective body 7, and is 4 mm, for example. An oil deficiency is present when the reception signal 12 is larger than a predefined level value PW. In the illustrated example, this level value is assumed to be one-half the maximum level of the reception signal. It is apparent that when the oil level is sufficient, the reception signal is small in all cases, and all characteristic curves achieve the largest possible reception signal (in the present case, 5 V) for an increasingly dropping oil level. An oil deficiency is recognized by comparing the reception signal to the predefined level value PW, an oil deficiency being present when the reception signal exceeds the level value PW.

Based on the various characteristic curves, it is apparent that the actual oil level at which an oil deficiency is determined is a function of the transmission power of the emitted light beam 10. If the light beam 10 emitted by the transmitter 8 is emitted at a transmission power of 10% during the monitoring operation, the characteristic curve intersects the switching threshold set by the level value PW at approximately 34% of the oil level. At 20% transmission power, the intersection point is at approximately 40%, and at a transmission power of 100% a deficient oil level is reached at a level of 46%.

This would result in refilling of oil from the reservoir 6 via the controller 4 and the solenoid valve 5, so that the oil level increases once more and the reception signal remains below the level value PW until the oil level once again drops.

The curves illustrated in FIG. 5 result if contamination of the optical system occurs during operation of the machine. It is apparent that the reception signal, which is based on a transmission power of 10%, reaches just to the level value P5 [sic; PW] for recognizing an oil deficiency. FIG. 6 illustrates the situation of a highly contaminated optical system. It is apparent here that a light beam used during the monitoring operation and having a transmission power of 10% is no longer suitable for reaching the level value PW. It is therefore provided to increase the transmission power with increasing contamination during the monitoring operation to ensure that an oil deficiency is reliably recognized.

For this purpose, however, it is necessary to determine the degree of contamination of the optical system. According to the invention, this takes place by carrying out the test operation described below as soon as an oil deficiency is recognized. To this end, the transmitter 8 transmits a first light beam at the maximum transmission power (100%), as the result of which a first reception signal is generated at the receiver 11. A difference is then formed between this first reception signal and a second reception signal, the second reception signal having been generated by a light beam at less than the maximum transmission power. In forming the difference between the two reception signals, the difference between the maximum levels of the respective reception signals is formed. The magnitude of the difference represents a measure of the degree of contamination of the optical system.

The reception signal of the monitoring operation, for which the oil deficiency has been determined, is advantageously used as the second reception signal during the test operation. However, it would also be conceivable to use a separate (test) light beam at a lower transmission power (10%, for example) during the test operation for generating the second reception signal.

The difference between the first reception signal at 100% transmission power and the second reception signal at 10% transmission power is illustrated as the difference signal D in FIGS. 4 through 6. It is apparent that the maximum level of the difference signal D becomes increasingly smaller with increasing contamination. Thus, for a clean optical system according to FIG. 4, the maximum level of the difference signal is approximately 4.7 V, for a slightly contaminated optical system drops to 3.2 V, and for a highly contaminated optical system is only 2.3 V. The difference signal D, which has been generated by reception signals having a different transmission power of the irradiated light beam, may therefore be regarded as a measure of the degree of contamination of the optical system. To save on operating costs, it makes sense for the light beam 10 emitted by the transmitter 8 to be emitted at a preferably low transmission power. However, the transmission power must be high enough that an oil deficiency is reliably recognized. By use of the test method described above, the transmission power may now be increased as a function of the magnitude of the difference between the first reception signal and the second reception signal. Thus, the situation in FIG. 5 represents the latest possible point in time at which the original transmission power of 10% has to be increased. For a degree of contamination which is the basis of FIG. 5, a transmission power of 20% is sufficient for reliable recognition of the oil deficiency.

In this way, the transmission power is progressively increased with increasing contamination. For a very high level of contamination, as illustrated in the diagram according to FIG. 6, an oil deficiency can be determined only when the light beam is irradiated at 100% transmission power during the monitoring operation. This is then also the latest point in time at which the optical system, in particular the conical tip 7a of the optical reflective body 7, must be cleaned. The correct time for cleaning the optical system may be determined, for example, in that the difference between the first reception signal and the second reception signal exceeds a predefined value.

The test operation is always routinely carried out when an oil deficiency is recognized. However, the test operation may also optionally be carried out when no oil deficiency is measured during the monitoring operation, but a set time period has elapsed since the last determined oil deficiency. Thus, for example, it is conceivable that when the machine is switched on, the optical system is already so heavily contaminated that the transmission power used is not adequate to generate a sufficiently large reception signal in the event of an oil deficiency. However, if a test operation is routinely carried out after a set time period (30 minutes or 60 minutes, for example), such contamination may be reliably recognized.

During operation of machines, such as a compressor in particular, it is customary for oil to have to be continually refilled. The time intervals between two oil refills may be recorded, and a test operation may be carried out when the time interval since the last oil refill, compared to the time intervals that have occurred in the past, exceeds a predefined amount. It is particularly suitable to average the time intervals that have occurred in the past, for example by taking into account the most recent five time intervals.

The invention claimed is:

1. A method for monitoring an oil level in a machine by means of an optical sensor, wherein a transmitter transmits a light beam into an optical system, and the light beam is reflected or refracted by the optical system, as a function of the oil level to be monitored, to a receiver, where a reception signal is generated, the light beam being emitted at a set transmission power during the monitoring operation, and an oil deficiency being recognized when the reception signal exceeds a predefined level value, characterized in that the transmission power of the light beam is settable between a minimum and a maximum transmission power, and a check of a degree of contamination of the optical system is carried out according to the following test operation as soon as an oil deficiency is recognized, the test operation having the steps of:

a. transmitting a first light beam with the transmitter at the maximum transmission power to generate a first reception signal at the receiver, b. transmitting a second light beam with the transmitter at a pre-set transmission power that is less than the maximum transmission power to generate a second reception signal at the receiver, c. determining the difference between the first reception signal and the second reception signal d. comparing the difference between the first reception signal and the second reception signal with reference values indicating the degree of contamination of the optical system.

2. The method according to claim 1, characterized in that the transmission power of the light beam is increased during the monitoring operation as a function of the magnitude of the difference between the first reception signal and the second reception signal.

3. The method according to claim 1, characterized in that the reception signal with which an oil deficiency has been recognized during the monitoring operation is used as the second reception signal during the test operation.

4. The method according to claim 1, characterized in that in the event of a determined oil deficiency, the oil level in the machine is increased by refilling with oil after carrying out the test operation.

5. The method according to claim 1, characterized in that the test operation is carried out even when no oil deficiency is measured during the monitoring operation, but a set time period has elapsed since the last determined oil deficiency.

6. The method according to claim 1, characterized in that the test operation is carried out even when no oil deficiency is measured during the monitoring operation, but a time interval since the last oil refill, in comparison to the time intervals between two oil refills that have occurred in the past, exceeds a set limit value.

7. The method according to claim 1, characterized in that for an average value of a predefined number of time intervals that have most recently occurred in the past is used for the comparison with the time intervals that have occurred in the past.

8. The method according to claim 1, characterized in that cleaning of the optical system is carried out when the difference between the first reception signal and the second reception signal is less than a predefined value.

9. A device for monitoring an oil level in a machine, having an optical sensor that is provided with a transmitter for transmitting a light beam into an optical system, and a receiver for receiving a reflected or refracted light beam from the optical system as a function of the oil level to be monitored, and for generating a reception signal, and an evaluation device for comparing the reception signal to a predefined level value, an oil deficiency being recognized when the reception signal exceeds the predefined level value, characterized in that a power control device is provided with the transmitter for setting the transmission power of the light beam between a minimum and a maximum transmission power, and the evaluation device is provided for checking a degree of contamination of the optical system according to the test operation described in claim 1.

* * * * *